United States Patent
Reinalda et al.

[11] Patent Number: 5,391,362
[45] Date of Patent: Feb. 21, 1995

[54] HIGH SURFACE AREA ZIRCONIA

[75] Inventors: Donald Reinalda; Anke Derking, both of Amsterdam, Netherlands

[73] Assignee: Shell Oil Company, Houston, Tex.

[21] Appl. No.: 668,847

[22] Filed: Mar. 13, 1991

[30] Foreign Application Priority Data

Jun. 5, 1990 [GB] United Kingdom ............... 9012524

[51] Int. Cl.$^6$ ............................................. C01G 25/02
[52] U.S. Cl. ........................................ 423/81; 423/84; 423/85
[58] Field of Search ............... 423/608, 81, 84, 85, 423/82; 502/208, 308

[56] References Cited

U.S. PATENT DOCUMENTS

| | | | |
|---|---|---|---|
| 2,871,138 | 1/1959 | Linnell et al. | 423/82 |
| 2,984,628 | 5/1961 | Alexander et al. | 252/313.1 |
| 4,400,568 | 8/1983 | Hofmann et al. | 502/208 |
| 4,427,575 | 1/1984 | Johnson et al. | 502/208 |
| 4,440,875 | 4/1984 | Kortbeek et al. | 518/728 |
| 4,521,528 | 6/1985 | Kovach | 502/208 |
| 4,746,497 | 5/1988 | Jenkins et al. | 423/82 |
| 4,822,575 | 4/1989 | Ngian et al. | 423/82 |

FOREIGN PATENT DOCUMENTS

| | | | |
|---|---|---|---|
| 2590887 | 12/1985 | France. | |
| 4530450 | 4/1966 | Japan | 423/608 |
| 59-35029 | 2/1984 | Japan | 423/608 |
| 63-156548 | 6/1988 | Japan | 423/85 |
| 1247339 | 7/1986 | U.S.S.R. | 423/84 |
| 686362 | 11/1986 | WIPO | 423/608 |

OTHER PUBLICATIONS

Grant and Hackn, "Chemical Dictionary", McGraw-Hill, N.Y., 1987, 5th Ed, p. 289.

*Primary Examiner*—John Niebling
*Assistant Examiner*—Brendan Mee

[57] ABSTRACT

The invention relates to a high surface area zirconia, having a surface area of above 125 m$^2$/g and preferably of above 200 m$^2$/g after calcination. The high surface area zirconia product of the invention can be prepared by mixing a zirconium salt solution with an alkali or ammonium compound, the zirconium hydroxide precipitate being aged in the presence of an oxygen acid of an element of group 5 or 6 of the Periodic Table of Elements and subsequently being calcined, optionally after a washing step. The preferred acid is phosphoric acid.

10 Claims, 1 Drawing Sheet

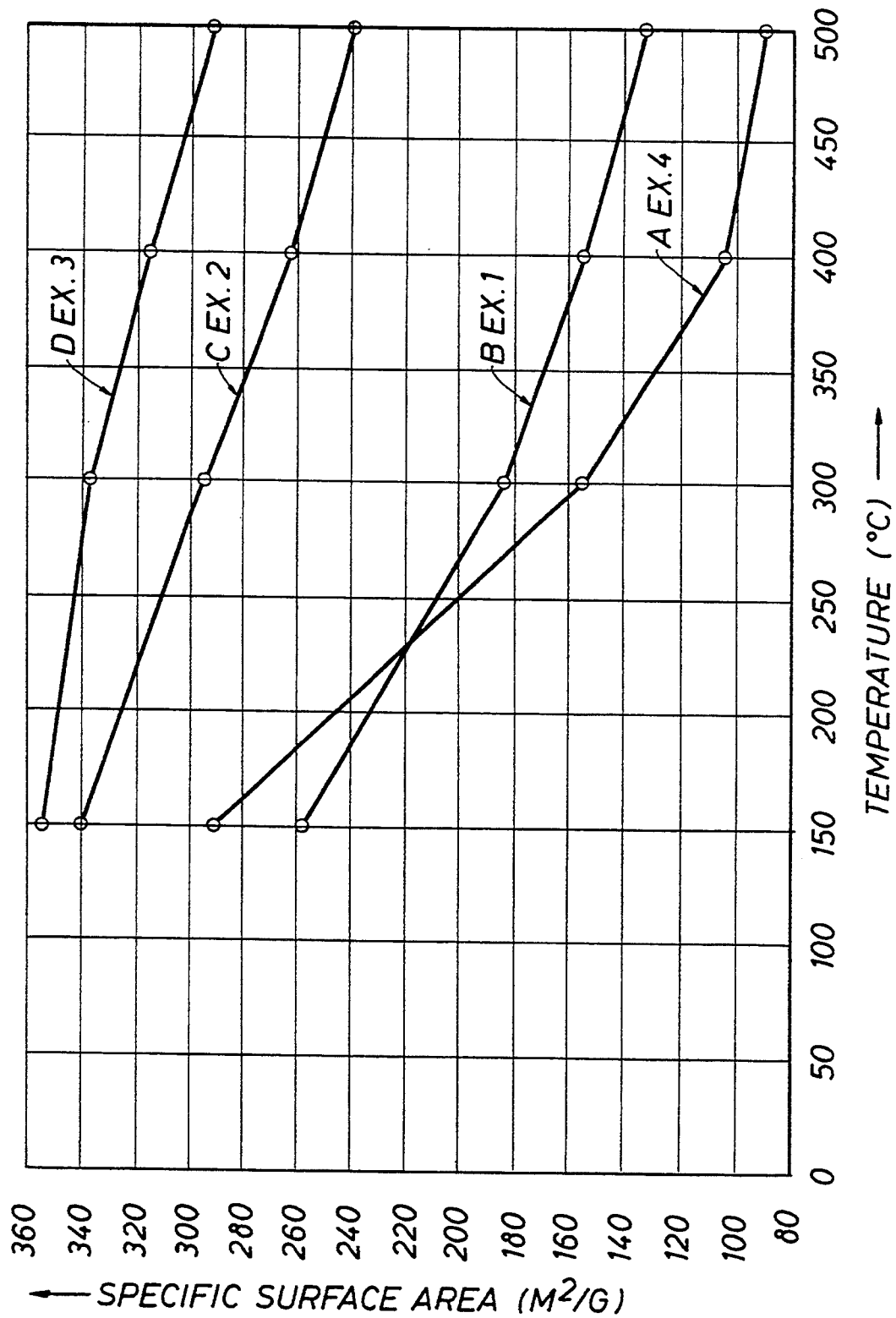

HIGH SURFACE AREA ZIRCONIA

Field of the Invention

The invention relates to high surface area zirconia, to a process for producing such high surface area zirconia and to a process for the production of hydrocarbons from synthesis gas using high surface area zirconia.

Background of the Invention

A process for the preparation of zirconia is known from French Patent No. 2,590,887 teaching the use of an additive to obtain a relatively high surface area zirconia, that still has a relatively high surface area after sintering, i.e., in the state wherein it is to be used as a catalyst or catalyst support. The additives used to this purpose are the oxides of silicon, rare earth metals and aluminum. The additives are used in an amount of about 1 to 10%, preferably 2 to 5%. A simple mixing process resulting into an intimate mixture of the zirconia and the oxides suffices. A coprecipitation of a zirconium oxide precursor with the precursors of the further elements mentioned, is also suitable. The preferred method is the impregnation of zirconium oxide with a solution of at least one salt precursor of the further oxides. The highest specific surface area reached ($m^2/g$) is 90 of a treatment at 400° C. Treatments at a higher temperature result into lower specific surface areas. One of the examples is a comparison and uses no additives. The specific surface area reached is 80 $m^2/g$ after a heat treatment at 400° C. and 20 $m^2/g$ after a heat treatment at 900° C. (The treatment takes 6 hours).

U.S. Pat. No. 4,440,875 teaches a process for the production of hydrocarbons from synthesis gas wherein a catalyst consisting of zirconium oxide promoted with at least one alkali metal compound is used. Preferably the zirconium oxide has a specific surface area in the range from 20 to 500 $m^2/g$ and is the alkali metal compound a potassium compound. The only example, however, describes just a specific surface area of 122 $m^2/g$ resulting from a previous calcination step carried out in air for 2 hours at 450° C. The catalyst is obtained by dissolving zirconium oxychloride in water and gradually adding ammonia to the solution until the pH value of the solution is in the range from 7 to 10. The precipitated zirconium hydroxide is separated from the solution by filtration and washed. The filtration residue is subsequently calcined from 1 to 24 hours in the air at a temperature in the range of from 300° C. to 1000° C.

The addition of an alkali metal compound to the catalyst improves the selectivity for butene.

The Journal of Physic. Chem. Institute 24-06-85 of the Soviet Union teaches the production of zirconium dioxide with a high specific surface area by treating a solution of zirconium nitrate with ammonia and washing the obtained gel, separating and drying it. It is then heated for 2 to 10 hours at 150° C. to 175° C. under a steam pressure of 6 to 10 atm. The specific surface area is 105 $m^2/g$.

U.S. Pat. No. 4,822,575 teaches a process for the preparation of zirconium compositions which on calcination form zirconia. The zirconium compositions are prepared by the addition of an ammonia source to an aqueous zirconium sulfate solution to give a solution pH in the value of from 0.1 to 2.5.

A general conclusion from the several disclosures is that up to now it was very difficult to reach a higher specific surface area after sintering of greater than 100 $m^2/g$. In general the surface area was 80 to 100 $m^2/g$.

Now a process has been found that yields a convenient method for a zirconia having a surface area of more than 125 $m^2/g$ after calcination, preferably more than 150 $m^2/g$ after calcination, more preferably more than 200 $m^2/g$ after calcination.

SUMMARY OF THE INVENTION

The invention relates to a high surface area zirconia characterized by a specific surface area of above 125 $m^2/g$ after calcination, preferably more than 150 $m^2/g$ after calcination, more preferably more than 200 $m^2/g$ after calcination. The invention also relates to a high surface area zirconia characterized by a specific surface area of above 125 $m^2/g$ after calcination, obtainable by mixing a zirconium salt solution with an alkali or ammonium compound, the precipitate being aged in the presence of one or more oxygen acids of an element of group 5 or 6 of the Periodic Table of Elements, and subsequently being calcined, optionally after a washing step, the oxygen acid preferably being phosphoric acid.

The invention also provides a process for producing high surface area zirconia products wherein zirconia is prepared from zirconium hydroxide by aging the zirconium hydroxide in the presence of an oxygen acid of an element of group 5 or 6 of the Periodic Table of Elements and subsequently calcining of at least 250° C., optionally after a washing step.

BRIEF DESCRIPTION OF THE DRAWING

The sole drawing shows the effect aging zirconium hydroxide in phosphoric acid has on the surface area of the as calcined material.

DESCRIPTION OF THE PREFERRED EMBODIMENTS

The instant zirconias are prepared by contacting a zirconium salt solution with a solution of an alkali or ammonium compound to form a precipitate of zirconium hydroxide. The precipitate is then aged in the presence of one or more oxygen acids of an element of group V or VI of the Periodic Table of the Elements. The term "alkali compound" as used herein refers to a compound that contains a hydroxy moiety or which upon hydrolysis with water generates hydroxyl ions. Thus, an alkali compound is a compound capable of generating hydroxyl ions in the presence of water.

Calcination is suitably carried out at elevated temperature, e.g. more than 250° C., preferably more than 300° C., more preferably more than 350° C., still more preferably between 450° C. and 550° C., for a period of at least 0.5 hour, preferably 1 to 4 hours, especially about 2 hours. The calcination is suitably carried out using an oxygen containing gas, especially air. Inert gases, e.g. nitrogen, helium, argon etc., may also be used.

Suitably, phosphor oxygen acids are used, especially orthophosphoric, metaphosphoric, hypophosphoric and pyrophosphoric acid. Preferably orthophosphoric acid is used.

As a solvent preferably water is used, however, other polar solvents can be used as well. Such as mixtures of water, ethanol, glycol and the like.

The preferred alkali or ammonium compound is ammonia, preferably in a 10% solution. Other alkali or ammonium compounds like for instance urea, hexamethylene tetraamine, (both generating hydroxyl ions by hydrolysis), ethanolamines, sodium and potassium hydroxide can be used too. In view of the character of the alkali compounds additional washing steps are necessary to wash the remainder out from the solids.

Preferably an aqueous 10% ammonia solution is used.

The zirconium hydroxide to be used in the process according to the present invention is suitably prepared by precipitating from a solution of a zirconium compound in water by mixing with an alkali or ammonium compound, followed by filtration.

The product obtained by the filtration can be dried prior to sintering although it is not strictly necessary. When it is dried before, care should be taken that the drying is not too strong since that would affect the properties of the product with regard to acid.

The preferred alkali is ammonia and the preferred aging time is $\frac{1}{2}$ to 5 hours, especially 0.8 to 1.2 hours. The precipitate suspension being aged preferably in 0.8 to 1.2 molar in $H_3PO_4$. The calcination is preferably performed at 450° to 550° C.

The invention further provides a process for the production of hydrocarbons from synthesis gas, characterized by using a catalyst on a zirconia support obtained according to the present process, or, alternatively by using the zirconia as a catalyst itself, either is the form as described above, or mixed with other oxides, e.g. oxides of manganese, zinc, copper and/or chromium. The zirconia of the present invention may also very suitably be used in the so-called iso-synthesis.

An essential difference with the prior art zirconia is that the amorphous structure is substantially maintained during the calcination. Further it appeared that the acidity of the present material is considerably higher as appears from the adsorption of an excess of ammonia and increase of the temperature at which desorption is measured.

The present absorption is about three times the amount of ammonia and the desorption occurs at 325° C. instead of 200° C. compared with prior art zirconia.

It further appeared that the aging time was of relative little influence provided that a certain minimum duration was obeyed. This minimum is about half an hour. An effective aging time is 24 hours, longer aging times do not result in an increase of surface area. Suitably 1 to 4 hours are used.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

EXAMPLE 1

1 Liter of 0.25M zirconia solution (produced by dissolving 66.10 g of $ZrO(NO_3)_2 \cdot xH_2O$ in demineralized water and diluting to 1 liter, resulting in an 0.25 molar solution) is brought into a glass reactor equipped with a double wall for temperature control and baffles to ensure effective mixing. While stirring, 10% aqueous ammonia is added dropwise at a rate of 1.35 ml/min. During the addition the pH value increases from 0.9 to 8.5. The solution is stirred for an other 0.5 hours whereby the pH value decreases to 8.4. The precipitate is filtered off and washed three times with 1 liter of demineralized water by suspending the precipitate again and filtering it.

Subsequently 109.4 g of the wet precipitate of LOI=90.62% is suspended in 100 ml of 0.25 molar $H_3PO_4$ solution and stirred for 24 hours. The material is then filtered off and washed on the filter with water. The solids obtained are dried at 120° C.

EXAMPLE 2

The process of example 1 is followed. After that the precipitate is obtained and has been washed and filtered 109.4 g of the wet material having a LOI=90.62% is suspended in 100 ml of 0.5 molar $H_3PO_4$ solution and is stirred for 24 hours. The solid material is filtered off and washed on the filter with demineralized water. The solids are dried at 120° C.

EXAMPLE 3

Following the method of example 1, the pH value during the ammonia addition increases to 8.6. After 0.5 hours of stirring the pH value decreases to 8.5. The precipitate is filtered off and washed three times with 1 liter of demineralized water by suspending the precipitate again and filtering off. Then 116.12 g of the wet material having an LOI=88.7% is suspended in 100 ml of 1 molar $H_3PO_4$ solution and stirred for 24 hours. The material is filtered off and washed on the filter with demineralized water. The solids obtained are dried at 120° C.

EXAMPLE 4

A zirconyl nitrate solution is produced by dissolving 71.04 g of zirconyl nitrate in demineralized water, the solution being diluted with demineralized water to 1 liter. This results into a 0.25M zirconium solution.

750 ml Of the zirconium solution are introduced in the 1 liter reactor and 50.0 g of urea are added.

Whilst stirring the solution is heated to 90° C. in about 1.5 hours. During the temperature increase the pH value decreases from 2.2 to 1.0 and increases then slowly. After about 16 hours the pH strongly increases to 6.5 (final pH value). After 24 hours the experiment is stopped. The precipitate is filtered off and washed three times with demineralized water by suspending the precipitate again in demineralized water and filtering it off. The solids are dried at 120° C. Evaluation of the products obtained.

The products obtained according to examples 1 to 4 are evaluated by heating the products for 1 hour on the temperatures indicated. The product of each example was heated at 150°, 300°, 400° and 500° C. The results are indicated in the figure, curve A indicates the product of example 4, curve B indicates the product of example 1, curve C indicates the product of example 2 and curve D indicates the product of example 3.

As is readily apparent, the aging under influence of phosphoric acid results into a considerably better surface area of the zirconia on aging.

What is claimed is:

1. A process for producing zirconia having a specific surface area of above 200 $m^2/g$, which comprises precipitating zirconium hydroxide from a solution of a zirconium compound in water by mixing said solution with an alkali compound selected from the group consisting of ammonia, urea, hexamethylene tetramine, ethanolamines, sodium hydroxide, and potassium hydroxide, washing the precipitate of zirconium hydroxide with water to remove alkali compound therefrom, aging the washed precipitate in the presence of a phosphoric acid, and subsequently calcining the aged precipitate at a temperature of about 250° to 550° C.

2. The process of claim 1 wherein the phosphoric acid is selected from the group consisting of orthophosphoric acid, metaphosphoric acid, hypophosphoric acid, pyrophosphoric acid and mixtures thereof.

3. The process of claim 2 wherein the phosphoric acid is orthophosphoric acid.

4. The process of claim 1 wherein the zirconium hydroxide is prepared by precipitating from a zirconyl or zirconium salt or ammonium zirconium carbonate solution in water.

5. The process of claim 1 wherein ammonia is used as alkali compound.

6. The process of claim 1 wherein the zirconium hydroxide is aged for ¼ to 5 hours at 0° to 100° C.

7. The process of claim 6 wherein the zirconium hydroxide is aged for 0.8 to 1.2 hours.

8. The process of claim 1 wherein the zirconium hydroxide is aged in 0.5 to 2 molar of acid.

9. The process of claim 1 wherein the calcining is performed at a temperature of above 300° C.

10. The process of claim 9 wherein the calcining is performed at a temperature of 450° to 550° C.

* * * * *